United States Patent [19]

Verbrugge

[11] 4,064,174

[45] Dec. 20, 1977

[54] PREPARATION OF 2-HALOCYCLOBUTANONES

[75] Inventor: Herman Verbrugge, Amsterdam, Netherlands

[73] Assignee: Shell Oil Company, Houston, Tex.

[21] Appl. No.: 662,173

[22] Filed: Mar. 1, 1976

[30] Foreign Application Priority Data

Jan. 6, 1976 United Kingdom .................. 329/76

[51] Int. Cl.$^2$ ..................... C07C 45/00; C07C 45/02
[52] U.S. Cl. ................. 260/586 C; 260/345.2; 260/346.22; 560/124; 260/514 G; 260/514 H; 260/586 F; 260/590 C; 260/590 FB
[58] Field of Search .......... 260/586 C, 514 H, 468 H, 260/345.2, 590 FB, 590 C, 346.2 R

[56] References Cited

U.S. PATENT DOCUMENTS

| 3,129,248 | 4/1964 | England | 260/586 C |
|---|---|---|---|
| 3,189,608 | 6/1965 | Martin | 260/586 |
| 3,288,854 | 11/1966 | Martin | 260/586 C |
| 3,390,185 | 6/1968 | Martin | 260/586 C |
| 3,646,150 | 2/1972 | Hall et al. | 260/586 C |
| 4,028,418 | 6/1977 | van den Brink et al. | 260/586 C |

FOREIGN PATENT DOCUMENTS

2,417,615  11/1914  Germany .......................... 260/514 H

OTHER PUBLICATIONS

Ghosey, "Tetra Lett", vol. 27, pp. 615–633 (1971).
Ghosey, "Tetra Lett", vol. 22, pp. 135–139 (1966).
Brady, "Synthesis", pp. 415–422, (1971).
Brady, "J. Org. Chem.", vol. 31, pp. 626–628, (1966).
Stevens, "J.A.C.S.", vol. 87, pp. 5257–5259, (1965).

*Primary Examiner*—Norman Morgenstern

[57] ABSTRACT

The preparation of a 2-halocyclobutanone by contacting a 2,2-dihaloalkanoyl halide with an ethylenically unsaturated compound at a temperature of at least 5° C in the presence of dispersed zinc or tin and certain alkanones is conducted by using a molar ratio of zinc (or tin) to 2,2-dihaloalkanoyl halide below 1.00, with the zinc (or tin) in the form of particles having a largest dimension of up to 0.05 mm, and adopting a temperature of up to 55° C.

12 Claims, No Drawings

PREPARATION OF 2-HALOCYCLOBUTANONES

The invention relates to an improved process for the preparation of a 2-halocyclobutanone wherein the halogen atom has an atomic number of up to 35, in which process a 2,2-dihaloalkanoyl halide, wherein the halogen atoms have an atomic number of up to 35, is contacted in the presence of an alkanone which has at least two branches in the carbon skeleton of the molecule and of which not more than one of the two carbon atoms attached to the carbonyl group is quaternary, with an ethylenically unsaturated compound at a temperature above 5° C in the presence of dispersed zinc or tin.

This process is described in U.S. Pat. No. 4,028,418 Gradual addition of dichloroacetyl chloride to a stirred solution of 2,3-dimethyl-2-butene in diisobutyl ketone containing suspended zinc particles resulted in a yield of 2-chloro-3,3,4,4- tetramethylcyclobutanone of 75%, calculated on starting dichloroacetyl chloride of 3.9, a molar ratio of dichloroacetyl chloride to 2,3-dimethyl-2-butene of 1.3, a temperature of 43° C, zinc in the form of turnings having a largest dimension of 0.841 mm and a starting concentration of 2,3-dimethyl-2-butene of 2.4 mol per liter of diisobutyl ketone. Modifying this experiment by reducing the molar ratio of zinc to dichloroacetyl chloride to 1.1 resulted in a decrease in yield to 51%, the theoretical yield still being 77.4% cf. Example VIII of U.S. Pat. No. 4,028,418.

The stoichiometric molar ratio of zinc or tin to dihaloalkanoyl halide being one, the excess of zinc or tin must be removed from the reaction mixture before further processing. This removal requires, for example, filtration or centrifugation. The liquid thus obtained may be washed with water to remove zinc halide or tin halide and excess of 2,2-dihaloalkanoyl halide. The 2-halocyclobutanones formed may be isolated in pure form by distillation of the washed liquid. Alternatively, the washed liquid may be heated with water in the presence of a base to effect ring contraction with formation of a cyclopropanecarboxylate. The solution of the cyclopropane-carboxylate obtained may be acidified by adding a strong mineral acid and the cyclopropanecarboxylic acid thus precipitated may be separated from the aqueous liquid, washed with water and dried.

The present invention avoids or facilitates the removal of solid material after termination of the reaction, while maintaining very good yields of 2-halocylobutanone.

SUMMARY OF THE INVENTION

The present invention may, therefore, be defined as relating to an improved process for the preparation of a 2-halocyclobutanone, wherein the halogen atom has an atomic number of up to 35, in which process A 2,2-dihaloalkanoyl halide, wherein the halogen atoms have an atomic number of up to 35, is contacted in the presence of an alkanone which has at least two branches in the carbon skeleton of the molecule and of which not more than one of the two carbon atoms attached to the carbonyl group is quaternary, with an ethylenically unsaturated compound at a temperature above 5° C in the presence of dispersed zinc or tin, the improvement comprising the use of a molar ratio of zinc or tin to 2,2-dihaloalkanoyl halide below 1.00, with the zinc or tin being in the form of particles having a largest dimension of up to 0.05 mm, at a temperature of up to 55° C.

The process may be conducted as described in previously mentioned U.S. patent, the disclosures of which are incorporated herein by reference. The preferred two methods comprise gradually adding the 2,2-dihaloalkanoyl halide to a stirred solution of the ethylenically unsaturated compound in the alkanone containing suspended zinc or tin particles, or, alternatively, in gradually adding the alkanone containing dispersed zinc or tin particles to a solution of the 2,2-dihaloalkanoyl halide and the ethylenically unsaturated compound in the alkanone. The conversion of the zinc or tin and the yield of 2-halocyclobutanone are favourably influenced when — after the said gradual additions have been finished — the reaction mixture is stirred for an additional period of time. However, the longer this period, the greater the chance will be that a brownish tarry material is formed. When — after this period — the reaction mixture is washed with water and the washing water is allowed to separate from the organic phase by settling, tarry material — if present — collects at the interface of the aqueous and the organic phase and on the wall of the vessel. This tarry material is slightly soluble in water and considerably hampers the isolation of the total amount of the organic phase and decreases the purity and darkens the colour of the cyclopropanecarboxylic acid when prepared by ring contraction of the 2-halocyclobutanone thus formed. The additional stirring period can be kept short, shorter than, for example, 1.5 hours, with complete conversion of zinc or tin and with formation of a non-troublesome amount of tarry material, if any, when the starting molar ratio of zinc or tin to 2,2-dihaloalkanoyl halide is up to 0.98. When this molar ratio is higher than 0.98 but lower than 1, long stirring times are required to achieve complete conversion of zinc or tin and tarry material is usually formed in troublesome amounts. The starting molar ratio is preferably at least 0.88. Application of a molar ratio equal to 1 produces a reaction mixture which, at the end of the stirring period, contains a small amount of zinc or tin and tarry material.

When the process according to the present invention is modified by adopting a temperature higher than 55° C, a considerable amount of tarry material is formed, which decreases the yield of 2-halocyclobutanone. Usually, the highest yields of 2-halocyclobutanones are obtained at a temperature in the range of from 15° C to 45° C, and particularly of from 30° C to 45° C.

The molar ratio of 2,2-dihaloalkanoyl halide to ethylenically unsaturated compound is not critical and may vary within wide limits. Molar ratios of 2,2-dihaloalkanoyl halide to ethylenically unsaturated compound increasing about 1 afford increasing yields of 2-halocyclobutanone, calculated on starting ethylenically unsaturated compound, but the yield hardly increases any further when the molar ratio is increases above 2. In view thereof, a molar ratio of 2,2-dihaloalkanoyl halide to ethylenically unsaturated compound in the range of from 1.25 to 2 is preferred.

The surprising effect mentioned above is particularly exerted by 2,2-dihaloacyl halides. Very good results are usually obtained with 2-haloalkanoyl halides, particularly with 2,2-dihaloalkanoyl halides.

Examples of such 2,2-dihaloalkanoyl halides are dichloroacetyl chloride, 2,2-dichloropropanoyl chloride, 2,2-dichlorobutanoyl chloride and the halides obtained when one or more of the chlorine atoms in these compounds are replaced by bromine atoms. Very good results have been obtained with dichloroacetyl chloride.

Ethylenically unsaturated compounds asymmetrical with respect to the double bond may form two different cyclobutanones, and alkynes asymmetrical with respect to the triple bond may form two different cyclobutenones, depending on the regiospecificity of the cycloaddition involved. For an explanation of the concept of "regiospecificity" see "Methoden der Organischen Chemie" (Houben-Weyl), 4th Edition (1971), Vol. IV/4, p. 143.

The unsaturated compounds may be hydrocarbons or may carry non-hydrocarbyl substituents such as, alkoxy, benzyloxy, oxo or ethoxycarbonyl groups, as is the case in, for example, isopropyl 3-methyl-2-butenyl ether, benzyl 3-methyl-2-butenyl ether, ethyl 2,3,5-trimethyl-2,4-hexadienoate and 6-methyl-5-heptene-2-one. However, substituted unsaturated compounds usually give cyclic compounds in yields less than, for example, 20 %, calculated on acyl halide. Unsubstituted unsaturated compounds usually afford the cyclic compounds in a higher yield and are, therefore, preferred. Alkenes having one carbon-carbon double bond are particularly preferred; they usually afford the cyclobutanones in a yield between, for example, 50 and 75%. The alkenes may have a straight or a branched chain and may have a cis or trans structure. Examples of alkenes are ethene, propene, 1-butene, cis-2-butene, trans-2-butene, isobutene, 2-pentene, 2-hexene, 3-hexene, 2-heptene, 3-heptene, 2-methyl-2-butene, 3-methyl-2-pentene, 3-methyl-3-hexene, 2,4-dimethyl-3-hexene, 2,3,4-trimethyl-2-pentene, 1-octene, 2-octene, 3-octene, 1-nonene, 1-decene, 1-dodecene, 1-tetradecene, 1-pentadecene, 1-hexadecene, 1-eicosene, 1-docosene, cyclobutylethene, cyclopentylethene, cyclohexylethene and 3-phenyl-1-propene. Very good results have been obtained with 2,3-dimethyl-2-butene and 2-methyl-2-pentene.

Among the ethylenically unsaturated compounds having two carbon-carbon double bonds per molecule 2,5-dimethyl-2,4-hexadiene reacts stereospecifically with monochloroketene to give trans-2-chloro-4,4-dimethyl-3-(2-methyl-1-propenyl) cyclobutanone and trans-2-chloro-3,3-dimethyl-4-(2-methyl-1-propenyl)cyclobutanone with a very high selectivity. For an explanation of the concept of "stereospecificity" see "Methoden der Organischen Chemie" (Houben-Weyl), 4th Edition (1971), Vol. IV/4, p. 143. The importance of this stereospecificity is explained further below. When the unsaturated compound has two carbon-carbon double bonds one of which is deactivated — for example by a chlorine atom — and the other is not, the latter enters into a cyclo-addition reaction. This is the case with, for example, ethyl 2,3,5-trimethylhexa-2,4-dienoate.

Unsaturated compounds containing an allenic structure yield alkylidenecyclobutanones. Examples of allenic unsaturated compounds are allene, 1,2-butadiene, 2,3-pentadiene, 2,4-dimethyl-2,3-pentadiene, 3,5-diethyl-3,4-heptadiene, 5-methyl-1,2-hexadiene, 2,8-dimethyl-4,5-nonadiene, 3-nonyl-1,2-dodecadiene, 1,2-pentadecadiene, allenylbenzene and tetraphenylallene.

When the two double-bonded carbon atoms in the ethylenically unsaturated compound form part of a ring of atoms, bicyclic compounds containing a cyclobutanone ring are formed. The starting cyclic compound may be, for example, five-, six-, seven-, or eight-membered, may be substituted or unsubstituted and may have a second carbon-carbon double bond. One of the members of the ring may be an oxygen atom. Examples of substituents are halogen atoms not bound to a double-bonded carbon atom, and alkyl groups. Examples of cyclic unsaturated compounds are cyclohexene, cycloheptene, cyclooctene, 1,2-dimethylcyclopentene, 2-methylcyclohexene, 3-methylcyclohexene, 2,5-dimethylfuran, indene, 2,3-dimethylindene and 2H-3,4-dihydropyran.

Examples of alkynes are propyne, 1-butyne, 2-butyne, 1-pentyne, 2-pentyne, 1-hexyne, 1-heptyne, 1-dodecyne, 2-methyl-1pentyne, phenylethyne and 3-phenyl-1-propyne.

The double- and triple-bonded carbon atoms in the ethylenically unsaturated compound and the alkyne, respectively, may not carry any deactivating substituents, such as halogen atoms, carboxyl or esterified carboxyl groups, because such substituted unsaturated compounds hardly form any cyclic compounds, if at all.

The novel process cannot be conducted in the absence of a solvent, because zinc chloride and tin chloride are only sparingly soluble, if at all, in the unsaturated compound. The solvent should not react with the compounds involved in the novel process; therefore, N,N-dimethylformamide, tetrahydrofuran, dioxane and dimethoxyethane are unsuitable. The solvent should promote the present cycloaddition; dimethyl sulphoxide and tetrahydrothiophene 1,1-dioxide are unsuitable, because they give a complicated mixture of compounds in which no cyclic compounds can be detected. The solvent should dissolve the zinc halide or tin halide formed; tetrachloromethane and hydrocarbons are therefore unsuitable.

Alkanones are the most attractive solvents found thus far, because high yields of cyclic compounds are obtained therein at concentrations of the acyl halide far above 1 mol/l. This particularly applies to alkanones which have at least two branches in the carbon skeleton of the molecule and of which not more than one of the two carbon atoms attached to the carbonyl group is quaternary. Diisobutyl ketone and methyl tert-butyl ketone are the preferred alkanones. In alkanones the acyl halide is partly converted into cyclic compounds and partly into polymers, whilst the balance remains unchanged. In actone, much polymer is formed - originating from the acyl halide and the unsaturated compound - resulting in a low selectivity to cyclic compounds. The selectivity to a compound is defined as the yield of this compound, calculated on the acyl halide converted. In methylethyl ketone, too, some polymer is formed, but less than in acetone; this polymer also originates from the acyl halide and the unsaturated compound. In methyl isobutyl ketone some polymer is formed as well, but only from the acyl halide. Little or very little polymer is formed in diisobutyl ketone and methyl tert-butyl ketone.

The yield of cyclic compounds decreases according as higher concentrations of the acyl halide in a alkanone are applied. These yields, however, are still very high at concentrations up to 15 and particularly up to 10 mol per liter of alkanone. In view of this, the acyl halide is preferably applied in a concentration in the range of from 1 to 15 mol, and particularly of from 3 to 10 mol per liter of the alkanone. The yield rapidly decreases with increasing concentrations of the unsaturated compound above 15 mol/l, irrespective of the acyl halide concentration, the zinc halide and tin halide formed becoming less and less soluble in the surrounding liquid. At concentrations increasing above 40 mol/l these halides are hardly soluble if at all and, consequently, hardly any or no cyclic compounds are formed.

Substituted cyclopropanecarboxylic esters are very suitable for use as insecticides, because they combine a high insecticidal activity with a low mammalian toxicity.

Thus, the present invention also relates to a process for the preparation of a cyclopropanecarboxylic acid in which the carbon atom carrying the carboxyl group also carries a hydrogen atom, by heating a 2-halocyclobutanone, prepared according to the present invention, with water in the presence of a base and converting the cyclopropanecarboxylate obtained into the corresponding acid to be used in preparing insecticidal esters.

The following Examples further illustrate the invention. The solvent used consisted of diisobutyl ketone containing 4,6-dimethyl-2-heptanone.

EXAMPLE I

Experiments 1-12 (see Table) were conducted in a 1-liter cylindrical flask provided with a turbine stirrer and baffles. Experiments 4, 5, 6, 7, 9, 10 and 11 are according to the invention, experiments 1, 2, 3, 8 and 12 are not. In all experiments a starting amount of 0.5 mol of 2,3-dimethyl-2-butene was used.

Experiment 1 was conducted as follows. The flask was charged, at a temperature 22° C, with 220 g of diisobutyl ketone (DIBK, see column 2 of Table), 3.25 mol of zinc particles having a largest dimension between 1.0 and 1.5 mm (see column 5), 0.5 mol of 2,3-dimetyl-2-butene (DMB), 0.017 mol of dichloroacetyl chloride (DCAC), 0.0005 mol of ammonium chloride and 0.00005 mol of sodium iodide. The diisobutyl ketone and 2,3-dimethyl-2-butene had a purity of more than 95%, and more than 99%, respectively. The zinc was kept homogeneously suspended by applying a stirrer speed of 500 revolutions per minute. Then, 0.5 mol of dichloroacetyl chloride was added at a temperature of 40° C (see column 8) over a period of one hour (see column 7). The reaction mixture thus formed was stirred for a further period of one hour (see column 9). The molar ratios of zinc to dichloroacetyl chloride and of dichloroacetyl chloride to 2,3- dimethyl-2-butene, derived from the amounts stated above, are given in columns 3 and 4, respectively.

The suspension obtained was separated by filtration, the zinc filtered off was washed with 50 ml of diisobutyl ketone, the washing liquid was mixed with the filtrate, the combined liquids were stirred with 100 ml of water, the mixture was allowed to separate by settling into an aqueous and an organic phase, the organic phase was isolated and mixed with 100 ml of water, the mixture was allowed to separate by settling into an aqueous and an organic phase, the organic phase was isolated and mixed with 763 ml of an 8%w aqueous caustic soda solution, stirring was continued for one hour, the mixture was allowed to separate by settling into an aqueous and an organic phase, the aqueous phase was isolated and acidified by adding 122 ml of 36%w aqueous hydrochloric acid, stirring was continued for one hour, the precipitated 2,2,3,3-tetramethylcyclopropanecarboxylic acid (TMCA) was filtered off (the filtrate had a pH below 1), washed three times with 1 liter of water and dried under a pressure of 10 cm Hg at a temperature of 40° C. The acid content of the dried precipitate was 99%w (TMCA, see column 14) and the yield of this acid (TMCA, see column 13) was 77%, calculated on starting 2,3-dimethyl-2-butene.

Experiments 2 and 3 were conducted in the same way as experiment 1, but in the absence of ammonium chloride and sodium iodide, the reaction time after the addition of dichloroacetyl chloride and the period of addition of dichloroacetyl chloride in experiments 2 and 3 were as stated in columns 9 and 7 of the Table, respectively.

Experiments 4, 5, 6, 7 and 8 were conducted in the same way as experiments 2 and 3. The details are stated in the table; the zinc particles had a largest dimension below 0.01 mm, see column 5. The diisobutyl ketone used in experiments 6 and 7 had a purity of 89 and 90%, respectively. At the end of experiments 4, 5, 6 and 7 the reaction mixture was free from dispersed zinc, see column 10, indicating that the zinc had been fully converted. The conversions of 2,3-dimethyl-2-butene and dichloroacetyl chloride are stated in columns 11 and 12, respectively. The yields of 2,2,3,3-tetramethylcyclopropanecarboxylic acid, presented in column 13, are slightly higher than that obtained in experiment 2. In the experiments 6 and 7 less brownish tarry material was formed than in the experiments 4 and 5 and the yield and purity of the TMCA formed were higher. The mixture obtained at the end of experiment 8 contained dispersed zinc and the yield of 2,2,3,3-tetramethylcyclopropanecarboxylic acid was only 49%, the molar ratio of zinc to dichloroacetyl chloride being 1.5.

Experiment 9 was conducted as follows. The flask was charged, at a temperature of 22° C, with 258 g of diisobutyl ketone, 0.5 mol of 2,3-dimethyl-2-butene and 0.85 mol of dichloroacetyl chloride. Then, a suspension of 0.5 mol of zinc particles having a largest dimension below 0.01 mm in 50 ml of diisobutyl ketone, was added at a temperature of 20° C over a period of 12 hours (see column 6). The mixture thus formed was stirred for a further period of one hour (see column 9). Experiments 10 and 11 were conducted in a similar way; the differences are indicated in the table. In the experiments 9 and 10 less brownish tarry material was formed than in experiment 11 and the yield and purity of the TMCA formed were higher.

The reaction mixtures obtained at the end of experiments 9 and 10 contained a small amount of dispersed zinc; the mixture obtained at the end of experiment 11 was free from dispersed zinc. The yields of acid presented in column 13, are of the same order of magnitude as those obtained in experiments 4, 5, 6 and 7.

Experiment 12 is comparable to experiment 10, but was conducted at a temperature of 60° C. The reaction mixture became black due to the formation of a considerable amount of tarry material.

TABLE

| 1 | 2 | 3 | 4 | 5 | 6 | 7 | 8 | 9 | 10 | 11 | 12 | 13 | 14 |
|---|---|---|---|---|---|---|---|---|---|---|---|---|---|
| | | | | Size of zinc particles, | Period of addition, h, of | | Temp., | Reaction time after addition of zinc or | Conversion, %, of | | | TMCA | |
| Exp. No. | DIBK g | Molar ratio | | | | | | | | | | yield, | purity, |
| | | Zn:DCAC | DCAC:DMB | mm | zinc | DCAC | ° C | DCAC, h. | zinc | DMB | DCAC | % | %w |
| 1* | 220 | 3.8 | 1.7 | 1.0–1.5 | — | 1 | 40 | 1 | n.d.** | n.d. | n.d. | 77 | 99 |
| 2* | 220 | 3.8 | 1.7 | 1.0–1.5 | — | 1 | 40 | 17 | 25 | n.d. | n.d. | 74 | 98 |
| 3* | 220 | 3.8 | 1.7 | 1.0–1.5 | — | 0.5 | 40 | 1 | n.d. | n.d. | n.d. | 67 | 97 |

TABLE-continued

| Exp. No. | DIBK g | Molar ratio Zn:DCAC | Molar ratio DCAC:DMB | Size of zinc particles, mm | Period of addition, h, of zinc | Period of addition, h, of DCAC | Temp., °C | Reaction time after addition of zinc or DCAC, h. | Conversion, %, of zinc | DMB | DCAC | TMCA yield, % | TMCA purity, %w |
|---|---|---|---|---|---|---|---|---|---|---|---|---|---|
| 4 | 248 | 0.97 | 1.5 | <0.01 | — | 6 | 30 | 16 | 100 | 92 | 97.5 | 75 | 93 |
| 5 | 248 | 0.88 | 1.7 | <0.01 | — | 7 | 30 | 16 | 100 | 95 | 94 | 77 | 90 |
| 6 | 248 | 0.97 | 1.5 | <0.01 | — | 5 | 40 | 1 | 100 | 90 | 95 | 78 | 99 |
| 7 | 168 | 0.89 | 1.8 | <0.01 | — | 5 | 40 | 1 | 100 | 96 | 87 | 81 | 99 |
| 8* | 258 | 1.5 | 1.0 | <0.01 | — | 3 | 40 | 2 | n.d. | n.d. | n.d. | 49 | 99 |
| 9* | 258 | 1.0 | 1.7 | <0.01 | 12 | — | 20 | 1 | 88 | 95 | 91 | 78 | 95 |
| 10* | 258 | 1.0 | 1.7 | <0.01 | 2.5 | — | 40 | 2 | 92 | 97 | 95 | 80 | 99 |
| 11 | 258 | 0.88 | 1.7 | <0.01 | 8 | — | 30 | 16 | 100 | 97 | 94 | 77 | 91 |
| 12* | 258 | 1.0 | 1.7 | <0.01 | 3 | — | 60 | | n.d. | n.d. | n.d. | n.d. | n.d. |

*not according to the invention.
**n.d. = not determined.

EXAMPLE II

A 500-l cylindrical, glass-lined reactor provided with a gate stirrer was charged, under nitrogen, with 220 kg of diisobutyl ketone having a purity of 90% and 1.05 kmol of zinc particles having a largest dimension below 0.01 mm. The zinc particles were kept homogeneously suspended by applying a stirrer speed of 80 revolutions per minute. the suspension had a temperature of 40° C. Then, 0.037 kmol of dichloroacetyl chloride was added to the reactor. Subsequently, 0.655 kmol of 2,3-dimethyl-2-butene was added in one portion, after which 1.14 kmol of dichloroacetyl chloride was introduced over a period of 9.5 hours, the molar ratios of zinc to dichloroacetyl chloride and of dichloroacetyl chloride to 2,3-dimethyl-2-butene being 0.89 and 1.8, respectively. The reaction mixture thus formed was stirred for a further period of one hour, at the end of which the reaction mixture was free from metallic zinc.

Then, consecutively, the reaction mixture was cooled to a temperature of 25° C, 140 l of water was added (which caused a temperature increase to 35° C), stirring was continued for 30 minutes, the mixture was allowed to separate into an aqueous and an organic phase at a temperature of 30° C, the aqueous phase was removed (a sharp phase separation could be obtained, tarry material being absent), 140 l of water was added to the organic phase, stirring was continued for 30 minutes, the mixture was allowed to separate into an aqueous and an organic phase, the aqueous phase was removed, 1600 kg of a 5%w aqueous sodium hydroxide solution was added, stirring was continued for one hour at a temperature of 35° C, the mixture was allowed to separate into an aqueous and an organic phase, the organic phase was removed, the aqueous phase was acidified by adding 160 kg of 35%w aqueous hydrochloric acid, stirring was continued for 1 hour and the precipitated 2,2,3,3-tetramethylcyclopropanecarboxylic acid was filtered off. The filter cake obtained was stirred at a temperature of 60° C with 350 kg of n-hexane and 230 l of water, the mixture was allowed to separate by settling into an aqueous and an organic phase, the organic phase was isolated and washed first with 100 l of water and then with 40 l of water. The washed organic phase was flashed at a temperature of 40° C and a pressure of 0.2 bar until 210 kg of n-hexane had been flashed off. The residual liquid, which still contained 140 kg of n-hexane, was cooled with stirring to a temperature of 12° C, resulting — after a period of 2 hours — in crystallization of 2,2,3,3-tetramethylcyclopropanecarboxylic acid. The crystals precipitated were filtered off at a temperature of 12° C and the filter cake obtained was washed with 25 kg of n-hexane at a temperature of 12° C. The washed filter cake was dried at a temperature of 20° C and a pressure of 0.1 bar. The dried filter cake had a weight of 53.3 kg and a 2,2,3,3-tetramethylcyclopropanecarboxylic acid content of 98%, the yield being 56, 2%, calculated on starting 2,3-dimethyl-2-butene.

The three aqueous liquids obtained after washing with the above-mentioned quantities of 230 l, 100 l and 40 l of water were combined and the aqueous liquid thus obtained was stirred with 140 kg of n-hexane. The mixture formed was allowed to separate by settling, after which the organic phase was isolated and combined with the mother liquid obtained in the above-mentioned crystallization at 12° C. The mixture of the two organic liquids was boiled down until 25 kg of n-hexane was left. The residual liquid thus obtained was cooled with stirring to a temperature of 12° C, which caused crystallization of 2,2,3,3-tetramethylcyclopropanecarboxylic acid. The crystals precipitated were filtered off and the filter cake obtained was washed with 4.7 kg of n-hexane at a temperature of 12° C. The washed filter cake was dried at a temperature of 20° C and a pressure of 0.1 bar. The dried filter cake had a weight of 10 kg and a 2,2,3,3-tetramethylcyclopropanecarboxylic acid content of 98%, the yield being 10.5%. The total yield of this acid amounts to 66.7%.

I claim:

1. A process for the preparation of a 2-halocyclobutanone, wherein the halogen atom has an atomic number of up to 35, in which process a 2,2-dihaloalkanoyl halide, wherein the halogen atoms have an atomic number of up or 35, is contacted in the presence of an alkanone which has at least two branches in the carbon skeleton of the molecule and of which not more than one of the two carbon atoms attached to the carbonyl group is quaternary, with an ethylenically unsaturated compound at a temperature in the range of from about 5° to 55° C in the presence of dispersed zinc or tin in a molar ratio of zinc or tin to 2,2-dihaloalkanoyl halide below 1.00 and wherein the zinc or tin is in the form of particles having a largest dimension of up to 0.05 mm.

2. A process as claimed in claim 1, in which the starting molar ratio of zinc or tin to 2,2-dihaloalkanoyl halide is in the range of from 0.88 to 0.98.

3. A process as claimed in claim 1 in which the zinc or tin is used in the form of particles having a largest dimension of up to 0.01 mm.

4. A process as claimed in claim 1, which is conducted at a temperature in the range of from 15° C to 45° C.

5. A process as claimed in claim 1, in which the molar ratio of 2,2-dihaloalkanoyl halide to ethylenically unsaturated compound is in the range of from 1.25 to 2.

6. A process as claimed in claim 1, which is conducted by gradually adding the 2,2-dihaloalkanoyl halide to a stirred solution of the ethylenically unsaturated compound in the alkanone containing suspended zinc or tin particles.

7. A process as claim in claim 1, which is conducted by gradually adding the alkanone containing dispersed zinc or tin particles to a solution of the 2,2-dihaloalkanoyl halide and the ethylenically unsaturated compound in the alkanone.

8. A process as claimed in claim 1, in which the 2,2-dihaloalkanoyl halide is dichloroacetyl chloride.

9. A process as claimed in claim 1, in which the ethylenically unsaturated compound is an alkene.

10. A process as claimed in claim 9, in which the alkene is 2,3-dimethyl-2-butene.

11. A process as claimed in claim 1, in which the alkanone is diisobutyl ketone.

12. A process claimed in claim 11, in which the solvent is a mixture of diisobutyl ketone and 4,6-dimethyl-2-heptanone.

* * * * *